US008911770B2

(12) United States Patent
Grassi

(10) Patent No.: US 8,911,770 B2
(45) Date of Patent: Dec. 16, 2014

(54) DISSOLVABLE DIETARY SUPPLEMENT STRIP AND METHODS FOR USING THE SAME

(76) Inventor: Alessandra Grassi, Manhasset, NY (US)

( * ) Notice: Subject to any disclaimer, the term of this patent is extended or adjusted under 35 U.S.C. 154(b) by 324 days.

(21) Appl. No.: 12/818,692

(22) Filed: Jun. 18, 2010

(65) Prior Publication Data
US 2011/0150968 A1 Jun. 23, 2011

Related U.S. Application Data

(60) Provisional application No. 61/268,959, filed on Jun. 18, 2009.

(51) Int. Cl.
| A61K 9/70 | (2006.01) |
| A61K 9/00 | (2006.01) |
| A61K 31/525 | (2006.01) |
| A61K 33/30 | (2006.01) |
| A61K 33/32 | (2006.01) |
| A23L 1/00 | (2006.01) |
| A23L 1/05 | (2006.01) |
| A61K 31/4985 | (2006.01) |
| A61K 31/045 | (2006.01) |
| A23L 1/30 | (2006.01) |
| A61K 31/375 | (2006.01) |
| A61K 31/714 | (2006.01) |
| A61K 31/4188 | (2006.01) |
| A61K 31/14 | (2006.01) |
| A61K 33/34 | (2006.01) |
| A61K 31/355 | (2006.01) |
| A61K 31/197 | (2006.01) |
| A61K 31/455 | (2006.01) |
| A61K 31/44 | (2006.01) |
| A61K 33/22 | (2006.01) |
| A61K 33/06 | (2006.01) |
| A61K 31/685 | (2006.01) |
| A61K 33/24 | (2006.01) |
| A61K 33/18 | (2006.01) |
| A61K 31/07 | (2006.01) |
| A61K 31/34 | (2006.01) |
| A61K 31/015 | (2006.01) |
| A61K 31/195 | (2006.01) |
| A23L 1/304 | (2006.01) |
| A61K 31/51 | (2006.01) |
| A61K 33/26 | (2006.01) |
| A61K 31/593 | (2006.01) |
| A61K 31/4415 | (2006.01) |
| A61K 45/06 | (2006.01) |
| A23L 1/302 | (2006.01) |

(52) U.S. Cl.
CPC .............. $A61K\ 31/015$ (2013.01); $A61K\ 31/525$ (2013.01); $A61K\ 33/30$ (2013.01); $A23V\ 2002/00$ (2013.01); $A61K\ 33/32$ (2013.01); $A23L\ 1/0067$ (2013.01); $A23L\ 1/05$ (2013.01); $A61K\ 31/4985$ (2013.01); $A61K\ 31/045$ (2013.01); $A23L\ 1/3002$ (2013.01); $A23L\ 1/3006$ (2013.01); $A61K\ 31/375$ (2013.01); $A61K\ 31/714$ (2013.01); $A61K\ 31/4188$ (2013.01); $A61K\ 31/14$ (2013.01); $A61K\ 33/34$ (2013.01); $A61K\ 31/355$ (2013.01); $A61K\ 31/197$ (2013.01); $A61K\ 31/455$ (2013.01); $A61K\ 9/0056$ (2013.01); $A61K\ 31/44$ (2013.01); $A61K\ 9/7007$ (2013.01); $A61K\ 33/22$ (2013.01); $A61K\ 33/06$ (2013.01); $A61K\ 31/685$ (2013.01); $A61K\ 33/24$ (2013.01); $A61K\ 33/18$ (2013.01); $A61K\ 31/07$ (2013.01); $A61K\ 31/34$ (2013.01); $A61K\ 31/195$ (2013.01); $A23L\ 1/304$ (2013.01); $A61K\ 31/51$ (2013.01); $A61K\ 33/26$ (2013.01); $A61K\ 31/593$ (2013.01); $A61K\ 31/4415$ (2013.01); $A61K\ 45/06$ (2013.01); $A23L\ 1/302$ (2013.01)
USPC ............ 424/439; 424/443; 424/400; 424/472

(58) Field of Classification Search
USPC .......................... 424/442, 439, 443, 400, 472
See application file for complete search history.

(56) References Cited

U.S. PATENT DOCUMENTS

| 5,700,478 | A | * | 12/1997 | Biegajski et al. | ............. 424/434 |
| 5,712,309 | A | | 1/1998 | Finnin et al. | |
| 6,552,024 | B1 | | 4/2003 | Chen et al. | |
| 7,727,546 | B2 | | 6/2010 | Moneymaker et al. | |
| 2004/0247744 | A1 | | 12/2004 | Pearce et al. | |
| 2005/0136096 | A1 | * | 6/2005 | Davidson | ...................... 424/442 |
| 2006/0035008 | A1 | * | 2/2006 | Virgallito et al. | ............. 426/650 |
| 2007/0087036 | A1 | * | 4/2007 | Durschlag et al. | ............ 424/439 |

OTHER PUBLICATIONS

Borates, www.ima-na.org/borates, pp. 1-2.*

* cited by examiner

Primary Examiner — Frederick Krass
Assistant Examiner — Tracy Liu
(74) Attorney, Agent, or Firm — Leo G. Lenna; Sorell, Lenna & Schmidt LLP

(57) ABSTRACT

A strip, which is both edible and dissolvable, is provided comprising a film and a dosage of at least 2% of the reference daily intake (RDI) of at least one dietary supplement for malnutrition or to prevent/treat alcohol induced hangovers. A method for treating malnutrition and/or preventing and treating alcohol-induced hangovers using a dissolvable orally administered strip.

17 Claims, 1 Drawing Sheet

DISSOLVABLE DIETARY SUPPLEMENT STRIP AND METHODS FOR USING THE SAME

CROSS-REFERENCE TO RELATED APPLICATIONS

This application claims priority to U.S. Provisional Application Ser. No. 61/268,959 filed Jun. 18, 2009, which is herein incorporated in its entirety by reference.

TECHNICAL FIELD

The present disclosure generally relates to dietary supplements, and more particularly to dietary supplements, such as vitamins and minerals, in an edible and dissolvable strip.

BACKGROUND OF THE INVENTION

Dietary supplements have been used to treat a host of medical conditions and physical symptoms. The means for administering such dietary supplements is often done in pill or liquid form in that such means are readily producible and easily transported and packaged.

Unfortunately pills and liquid forms of dietary supplements pose various problems in use. Dietary supplements in pill form can have a large physical size which is often necessitated by the multiple components contained in the dietary supplement which are needed to assure an adequate dosage of the desired dietary supplement components, e.g., meeting the recommended daily allowance of various vitamins, minerals and nutrients. The term "horse pill" has been coined by the use of such large size pills. The size of these pills can prove difficult to swallow and may deter their use.

In addition, certain compositions of dietary supplements can be used to treat malnutrition and lack of essential vitamins and minerals. Malnutrition in the daily diet of both young and old individuals can lead to severe, sometimes, irreversible health problems in individuals living in the United States and throughout the world. The use of pills to treat malnutrition may pose additional problems in that often where there is malnutrition there is also a shortage of clean drinking water. Therefore, pills and capsules that may require and/or assist the physical administration of the same by the drinking of potable water to consume the pill or capsule poses severe difficulties to their use. Also, often children and/or adults suffering from malnutrition have difficulties swallowing making pills/capsules impractical, even if clean drinking water is available.

As for liquids, dosage control is an issue. The provision of large bottles of a dietary supplement with instructions on daily dosage (often written in a foreign language to that of the administered population) poses the problem of potential overdose. Even if such liquids are provided with dosage information in the native language, many people of countries having severe malnutrition may also be illiterate, thus, obviating the purpose of any written dosage information on the bottle. Still further problems are the storage of unused dietary supplements that may expire sooner in the extreme temperature conditions found in countries having issues of malnutrition.

The use of pills or liquid forms of dietary supplements also pose challenges in situations wherein the dietary supplement is used to treat other than malnutrition. For example, the conspicuous consumption of a pill or the use of a physical dispensing means, e.g., a spoon to administer liquid forms of the same may deter people in certain social settings from the use of such means due to issues of personal privacy. Even in situations of treating malnutrition the use of a physical pill or liquid form may prove socially embarrassing for the treated person and as such other more discrete forms of administration would be desirable.

One further such situation can be when such a dietary supplement is used to treat a hangover. Hangovers which result from the over indulgence of alcohol are believed to have two basic causes, the diuretic effect of ethanol and the toxic effect of acetaldehyde on the body which is produced by the conversion of ethanol in the liver. Because the conspicuous use of a dietary supplement to treat a hangover may be socially undesirable it would be desirable to provide a means of administering such a dietary supplement in a manner that is not as overt as the use of a pill or liquid form of dietary supplement.

Orally dissolvable strips containing dietary supplements are a means to discretely treat such conditions as malnutrition and hangovers. In addition, orally dissolvable strips containing dietary supplements and/or essential vitamins can also be used to revitalize athletes, boost an individual's immune system, and deliver prescription medication.

In addition, vitamins and minerals that are taken via the digested tract are less efficient since a large amount of the vitamins and minerals taken are modified, activated, or inactivated before they enter the systemic circulation, or are left unchanged and excreted. That is, intestinal and hepatic degradation or alteration of a vitamin, mineral, drug or substance taken by mouth, after absorption, removes some of the active substance from the blood before it enters the general circulation. Thus, what is needed is a way of getting more of the vitamins and/or minerals administered into the general circulation.

The use of orally dissolvable strips poses additional problems in their use. For example, the strips are usually required to be thin in that such strips are often packaged in rolls with a backing material and the use of strip that is too thick can prevent effective rolling of the strip material and limit the doses available in a single package. This can cause problems in production and excessive cost in the desired product.

In addition, the use of strips that are thin results in a two-fold problem of the strips adhering to each other in certain physical situations such as excessive humidity, e.g., the excessive humidity that can be found in areas of the world that have issues of malnutrition, and secondly the inability to effectively contain an effective dose of dietary supplement in such a thin strip.

For all these reasons and more, what is needed is an inexpensive way for consumers to be able to fulfill their daily dietary needs and/or treat any issue such as malnutrition or hangover while avoiding the problems of excessive adherence of the strips and the inability to concentrate active ingredients on the strip so as to be effective.

The present invention provides an easy, inexpensive way to effectively delivering essential dietary supplements including vitamins and minerals without water in a pre-measured dosage more effectively. The present invention also overcomes the inherent problems with thin-film strips sticking together. The present invention is further described in the sections following hereafter.

SUMMARY OF THE INVENTION

The present invention provides dietary supplements in the form of an oral dissolvable strip for administration to a mammal, which is a significant source of at least one dietary supplement, such as a vitamin and/or a mineral; and a method of use thereof. Desirably, the dissolvable oral strip provides amounts of the dietary supplements sufficient to provide the reference daily intake (RDI), as further described below, for each dietary supplement and is easily stored, administered, and is inexpensive to manufacture.

The dietary supplement delivery system of the present invention comprises at least one orally soluble strip having at least one dietary supplement. The orally soluble strip being at least partially coated with powder to prevent the strip from adhering or sticking to other surfaces.

The orally soluble strip can be a starch pectin and/or cellulose-based strip that dissolve when placed in an oral cavity of a mammal thereby substantially bypassing the first pass metabolism. Substantially bypassing first pass metabolism delivers more of the vitamins and/or minerals of the strip to the mammal so that it can effectively be used by the mammal than customary digested dosages of the same. The dietary supplements of the soluble strip can be selected from the group consisting of: vitamin C, $B_1$, $B_2$, $B_3$, $B_6$, folic acid ($B_9$), $B_{12}$, $B_5$ (pantothenate), H (biotin), A, E, $D_3$, $K_1$, potassium iodide, cupric (sulfate anhydrous, picolinate, sulfate monohydrate, trioxide), selenomethionine, borate(s), zinc, calcium, magnesium, chromium, manganese, molybdenum, betacarotene, iron, lutein, lycopene, gamma-tocopherol, inositol, choline, PABA, trimethylglycine (anhydrous betaine), betaine hydrochloride, vitamin $K_2$ as menaquinone-7, lecithin, citrus biofiavinoids, and combinations thereof. The orally dissolvable strip is also coated with a powder that comprises at least one dietary supplement listed above and/or one or more of the following inactive ingredient, coloring agent, surfactant, flavoring agent, pharmaceutically acceptable filler, or fragrance.

The dietary supplement delivery system of the present invention can be configured so that the orally soluble strip is releasably mounted to a backing material in a package that is configured to dispense single servings of the orally soluble strips.

In one embodiment of the present invention, the dietary supplement delivery system is formulated to prevent and/or treat symptoms of alcohol-induced hangovers comprising at least one orally soluble strip comprising at least one dietary supplement selected from the group consisting of: thiamine (mononitrate), riboflavin, niacin (amide), vitamin B6, pantothenate (d-cal pantothenate), vitamin C (as calcium ascorbate), vitamin B-12 (as cyanocobalamin) and biotin, wherein the orally soluble strip is at least partially coated with powder to prevent the strip from adhering or sticking to other surfaces.

In particular, the dietary supplement delivery system formulated to prevent and/or treat symptoms of alcohol-induced hangovers comprises by weight:
about 200 mg to about 400 mg of Thiamine (mononitrate); about 5 mg to about 20 mg of Riboflavin; about 50 mg to about 100 mg of Niacin (amide); about 20 mg to about 40 mg of Vitamin $B_6$; about 15 mg to about 30 mg of Pantothenate (d-cal Panthothenate); about 100 mg to about 300 mg of Vitamin C; about 20 mg to about 40 mg of Vitamin B-12; about 20 mg to about 70 mg of Biotin; and mixtures thereto.

The dietary supplement delivery system formulated to prevent and/or treat symptoms of alcohol-induced hangovers of the present invention can be a single strip coated with powder as described or a plurality of strips stacked upon one another to provide a multi-stacked strip. The multi-stacked strip is designed to have a higher concentration of dietary supplement than a single strip, and can be used instead of multiple strips. To increase the concentration of the multi-stacked strip even more, as well as to prevent sticking of the strips to other surfaces, the multi-stacked strip is coated with powder containing additional active ingredients.

Also provided as part of the present invention is a method of supplementing the diet of a mammal and/or preventing and/or treating hangovers of a mammal comprising providing at least one orally soluble strip as described above and placing the strip in the oral cavity of a mammal so that it can dissolve. Once the strip is placed in the oral cavity of the mammal, the enzymes in the mouth (such as amalylaze) begin to dissolve the strip thereby releasing the vitamins into the salvia. The vitamins/minerals are to be directly absorbed through the mucosa membrane. This takes time. Therefore, the method designed to use multiple strips allots for a time delay between placing strips in the oral cavity so that the entire strip can dissolve in the mouth of the mammal prior to administering the next stripe. These steps can be repeated as necessary. For example, the method of the present invention designed to prevent and/or treat hangovers can be done before consuming alcohol, as well as, after alcohol has been consumed to better prevent and treat the symptoms of an alcohol-induced hangover.

The above-disclosed embodiments of the present invention are further described in greater detail in the Detailed Description of the Invention directly following.

DETAILED DESCRIPTION OF THE INVENTION

Figure 1:
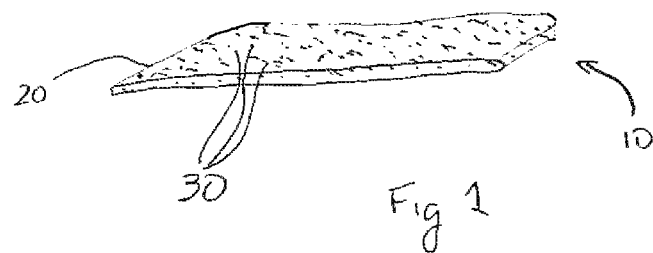
FIG. 1 shows a perspective view of a single dissolvable-coated strip of the prevent invention.

The present invention is directed to a delivery system for dietary supplements that is designed to overcome the problems of the prior art and to provide a quick and easy way to get enough vitamins/minerals or other active ingredients directly into the circulation system of a mammal whereby substantially bypassing first pass metabolism. This makes more vitamins/minerals readily available to the mammalian body and less loss to digestion. As further described below the dietary supplement delivery system uses oral strips comprising varying vitamins/minerals/actives and concentrations of the same. The physical and chemical properties of the dissolvable strip limit the concentration of vitamins, minerals and actives that can be included as part of the strip. Therefore, the present invention also coats the strip with a composition that can contain one or more vitamins, minerals and/or actives and thereby provides increased concentrations as well as, prevents the strips from sticking to one another in the package.

While the invention is described mainly as a delivery system to deliver vitamins and minerals as a dietary supplement that is designed to bypass first pass metabolism and enter quickly into the circulatory system of the mammal that is simply to assist the reader in understanding one particular use and in light of the specification. Upon understanding the aspects of the present invention it will be clear that the invention can be used for prescription and non-prescription (over-the-counter) drug delivery as well and are envisioned to be part of the invention.

Also, as used in the specification and including the appended claims, the singular forms "a," "an," and "the"

include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

The term "dietary supplement" was defined in the Dietary Supplement Health and Education Act (DSHEA) of 1994. In short, a dietary supplement is a product taken orally that contains a dietary ingredient intended to supplement the diet, to promote the health of the individual. The dietary ingredients may include, for example, vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. The DSHEA places dietary supplements in a special category under the general umbrella of foods, not drugs. In particular, if a product contains less than 2 percent of the reference daily intake (RDI) of a given dietary supplement, the product is not a "significant source" of that dietary supplement.

Dietary supplements can be in the form of liquid/powder as a concentrate/extract. The liquid concentrate/extract can be mixed with dissolvable carbohydrates to manufacture the dissolvable strips of the present invention. This allows a first level of saturation of one or more dietary supplement that makes up the strip itself. In order to manufacturer a dissolvable strip having a second level of saturation, the dissolvable strip can be powdered coated with the same or different dietary supplement. For example, the strips can be saturated with Vitamin B12 and then coated with Vitamin C in order to prevent a condition known as "crickets" which is a Vitamin C deficiency. The present invention therefore provides a vehicle for providing at least one essential dietary supplements in a portable convenient form that can be taken without water.

The term "vitamin" shall be understood herein to refer to any trace organic substance that is required in the human diet. For the purposes of the present invention, the term "vitamin" includes, without limitation, thiamin, riboflavin, nicotinic acid (niacinamide), pantothenic acid (D-calcium pantothenate), pyridoxine (vitamin B6), biotin, folic acid, folate, vitamin B12, lipoic acid, ascorbic acid, vitamin A, vitamin D, cholecalciferol (vitamin D3), vitamin E and vitamin K. Also included within the term "vitamin" are the coenzymes thereof. Coenzymes are specific chemical forms of vitamins. Coenzymes include thiamine pyrophosphates (TPP), flavin mononucleotide (FMM), flavin adenine dinucleotive (FAD), Nicotinamide adenine dinucleotide (AND), Nicotinamide adenine dinucleotide phosphate (NADP) Coenzyme A (CoA) pyridoxal phosphate, biocytin, tetrahydrofolic acid, coenzyme B12, lipoyllysine, 11-cis-retinal, and 1,25-dihydroxycholecalciferol. The term vitamin(s) also includes choline, camitine, and alpha, beta, and gamma carotenes.

The term "mineral" shall be understood herein to include macronutrients, micronutrients, inorganic substances, metals, and the like required in the human diet. The term "mineral" as used herein includes, without limitation, boron, calcium, chlorine, fluorine, iodine, iron, zinc, zinc lactate, selenium, sodium selanate, copper, iodine, magnesium, manganese, manganese chloride, manganese sulfate, molybdenum, nickel, phosphorus, potassium, chromium, tetrasodium pyrophosphate, Dicalcium phosphate dihydrate, sea salt and the like, and mixtures thereof.

Essential vitamins and/or minerals are vitamins and/or minerals that are required by the body to maintain proper health of an individual. For examples, the following are several essential minerals and vitamins and their associated function in the body.

Vitamin A promotes vision in dim light, mucous membranes, bones, teeth and skin.

Vitamins B—Thiamin keeps carbohydrate metabolism and nervous system in good condition.

Riboflavin takes care of the skin, and fat/protein/carbohydrate metabolism.

Niacin promotes effective use of oxygen by our cells, fat/protein/carbohydrate metabolism, and the nervous system.

Vitamin B6 is for protein metabolism.

Folate is the same as folic acid, which is good for red blood cell tissue growth and repair.

Vitamin B12 promotes new tissue growth, red blood cells, the nervous system and the skin.

Biotin metabolizes fat, protein and carbohydrates.

Pantothenic Acid aids in the metabolism of fat, protein and carbohydrates.

Vitamin C builds collagen, healthy gums, teeth and blood vessels.

Vitamin D is good for calcium absorption, bones and teeth.

Vitamin E protects cells from damage. Nut and vegetable oils, mangoes, blackberries, apples, broccoli, peanuts, spinach.

Vitamin K prevents blood clotting.

Calcium builds strong bones and teeth, muscles and nerves, and prevents blood from clotting.

Chloride aids in digestion. It works with sodium to maintain fluid balance. Salt.

Chromium assists in metabolism of carbohydrates.

Copper is good for the blood cells and connective tissues.

Fluoride protects the tooth enamel.

Iodine promotes thyroid function.

Iron brings oxygen in blood and is good for metabolizing energy.

Magnesium protects the bones, nerve and muscle function.

Manganese is good for the bones, connective tissues and fat/carbohydrate metabolism.

Molybdenum helps in nitrogen metabolism.

Phosphorus metabolizes energy.

Potassium keeps acids balanced.

Selenium works with Vitamin E to protect cells and body tissue.

Sodium keeps the fluid balanced and the nervous system in good condition.

Zinc aids in wound healing, growth, appetite and sperm production.

The term "dietary ingredient" shall be understood herein to include vitamins, minerals, herbs or other botanicals, amino acids, and substances such as enzymes, organ tissues, glandulars, and metabolites.

The term "dietary supplement" shall be understood herein to include any product taken by mouth that contains a "dietary ingredient," as defined above, which is intended to supplement the diet. Dietary supplements can be in the form of extracts/concentrates and may be used to manufacture concentrated dissolvable strips of the present invention.

The term "reference daily intake" (RDI) shall be understood herein to refer to the estimated daily intake values for vitamins, minerals, and other dietary ingredients established by the FDA. For example, the RDI for vitamin B1 is about 1.1 mg; the RDI for vitamin B6 is about 2.0 mg; the RDI for vitamin A is about 5,000 International Units (IU); the RDI for vitamin D3 is about 400 IU; the RDI for vitamin E is about 30 IU; the RDI for niacinamide is about 18 mg; the RDI for vitamin B12 is about 6 micrograms (μg); the RDI for D-calcium pantothenate is about 10.0 mg; the RDI for sodium selanate is about 70 μg; the RDI for zinc lactate is about 15 mg; the RDI for magnesium sulfate is about 400 mg; and the RDI for sea salt is about 2300 mg. Other RDI values can be found in the listing provided by FDA.

In general, the expression "significant source," when referring to a product including at least one dietary supplement, shall be understood to mean that the product includes at least 2% of the RDI for the dietary supplement(s) included therein. In some cases, much more than the RDI of a particular vitamin/mineral can be used to manufacturer the dissolvable strips depending on the end user of the dissolvable strip. The strips may contain multiple dosages of one or more essential mineral and/or vitamin in a coating or powder based coating of the strip. As further described below the coating/powdered coating can be used to prevent the sticking of the strips.

As stated above, the present invention is directed to a dietary supplement delivery system for a mammal that includes a dissolvable oral strip comprising concentrated dosages of vitamins and/or minerals as part of the dissolvable strip and is powder coated to avoid sticking of one strip to another. The powder used to coat the dissolvable strip can include one or more vitamins/minerals further concentrating the dosage provided in each strip or plurality of strips. By way of example and without limitation, a starch, pectin, and/or cellulose based strip or film that adheres to and dissolves in a mouth of a mammal can be used to help with malnutrition, medical conditions and prevent and/or treat the symptoms associated with alcohol-induced hangovers. A strip comprising the dietary supplement of the present invention will readily dissolve in salvia since the enzymes that are essential for breaking down starch-based compositions, the "glue" of the strip and therefore release the active ingredients of the composition.

The orally dissolvable strip formulation is made utilizing conventional film formulation processing and technology. The preferred film formulation is a starch-based film formulation or matrix. Other film formulation matrixes can be utilized such as pectin and other film bases (cellophane tape).

In one embodiment of the present invention, a strip is provided which is both edible and dissolvable comprising a thin starch-based film and a dosage of at least 2% of the reference daily intake (RDI) of at least one dietary supplement. It is envisioned that the strips of the present invention are small enough to fit in the mouth of a man, woman, and child and is ingestible/absorbable without water. Since the strips of the present invention are dissolvable in salvia, water is not necessary to digest the strip. In contrast to taking pills or capsules, the risk of choking when using the strip delivery system is drastically reduced since it is designed to quickly dissolve upon contact with saliva. It is further envisioned that the strips of the present invention will be easy to use, inexpensive, and portable.

In particular, the strip of the present invention will dissolve either upon contact with the tongue, the oral mucosa (epithelium lining the inside of the mouth), or any saliva present in the oral cavity. It is envisioned that the strip of the present invention may be made from any film known in the art which is both edible and dissolvable, such as, for example, pullan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein, polysaccharides, natural gums, polypeptides, polyacrylates, starch, karaya gum, gelatin, ellulose ethers; modified starches; natural gums; gelatins; edible polymers; hydrocolloid flours; seaweed extracts; land plant extracts, and mixtures thereof.

When strips fabricated from the film of the invention are stacked together with the surface of one strip in contact with the surface of an adjacent strip even mild adhesion of the strips to each other can interfere with the withdrawal of an individual strip from the stack of strips. However, when a multi-stacked strip is manufactured only the final multi-stacked strip is coated. That is, if a single strip is used it can be coated with powder to prevent sticking to adjacent strips. If a multi-strip delivery system is needed to provide the particular concentration of the active ingredients, (i.e. vitamins, minerals, drug etc.), the stickiness of each strip is used to hold the plurality of strips together as a single unit wherein the final stacked strip is powdered so as to prevent sticking of one multi-strip plurality system to the next.

As shown in FIG. 1, the single dissolvable strip delivery system 10 comprises a single strip 20 made from material dissolvable in saliva and is powdered with a plurality of particles 30 that coat the strip. The coated strip, as discussed above, prevents the strip from sticking to an adjacent strip. As also stated above, the particles 30 can be in granular or powder form and may or may not contain active ingredients. This aids in further concentrating the strips with active ingredients.

Figure 2:
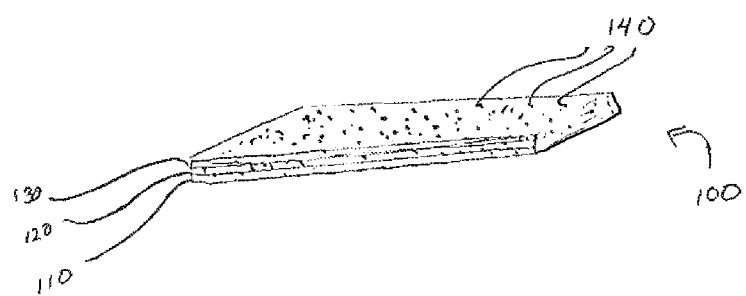
FIG. 2 shows a perspective view of a stacked dissolvable-coated strip of the prevent invention.
Figure 3:
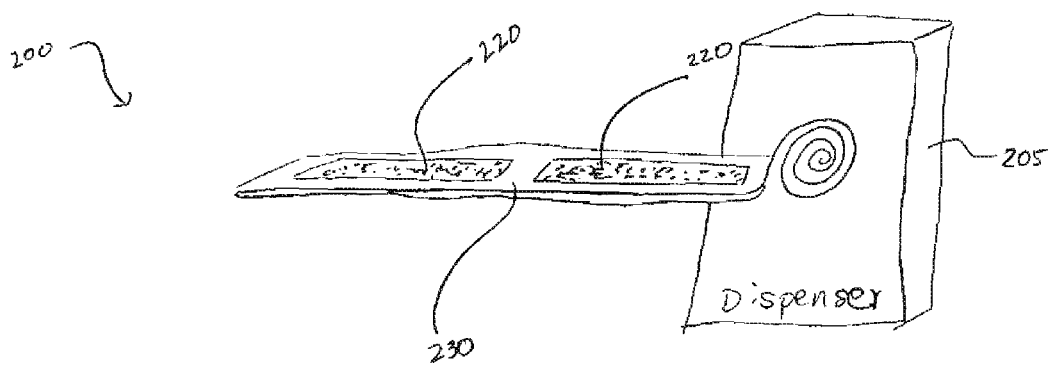
FIG. 3 shows a perspective view of a dispenser containing a plurality dissolvable-coated strip of the invention present attached to a backing material.

FIG. 2 shows a perspective view of a stacked strip 100 comprising multiple single strips 110, 120, 130 wherein the final stacked strip is coated with particles 140 that prevent sticking to other surfaces. Finally, FIG. 3 shows perspective view of a dispenser system 200 including a dispenser with a backing material 230 wound within. The dispenser 205 is configured so as to hold a pre-determined amount of backing material 230 in a coiled fashion that can be dispensed as needed. Releaseably attached to the backing 230 is a plurality of strips 220 that can be pulled away from the backing and administered. The strips attached to the backing material 230 can have less coating particles on the underside surface so that they have a higher degree of stickiness than the higher coated top surface of the strips. This gives the added feature of releaseably attaching to the backing 230 just enough to hold them in place but not sticking to the backing as it is wound into the coil. The backing 230 has a waxy, smooth surface so as to prevent permanent sticking.

In one embodiment of the present invention, the dietary supplement(s) is/are selected from the group consisting of: vitamin C, $B_1$, $B_2$, $B_3$, $B_6$, folic acid ($B_9$), $B_{12}$, $B_5$ (pantothenate), H (biotin), A, E, $D_3$, $K_1$, potassium iodide, cupric (sulfate anhydrous, picolinate, sulfate monohydrate, trioxide), selenomethionine, borate(s), zinc, calcium, magnesium, chromium, manganese, molybdenum, betacarotene, iron, and combinations thereof. However, it is envisioned that the strips of the present invention may include any known dietary supplements that are compatible with this mode of delivery. Additional dietary supplement(s) include but are not limited to lutein, lycopene, gamma-tocopherol, inositol, choline, PABA, trimethylglycine (anhydrous betaine), betaine hydrochloride, vitamin $K_2$ as menaquinone-7, lecithin, citrus bioflavinoids, and combinations thereof.

In another embodiment of the present invention, the strips include the dietary supplements which are most deficient in the diets of individuals of a given demographic, such as Indians, Haitians, middle-eastern natives for example. Special formulations can be produced in order to deal with region-related illnesses and diet deficiencies. In the alternative the strips of the present invention can be used domestically to fight vitamin/mineral deficiencies in poor and uneducated areas.

In yet another embodiment of the present invention, the strips of the present invention include at least one inactive ingredient selected from the group consisting of coloring agent, surfactant, flavoring agent, pharmaceutically acceptable filler, and fragrance. It is envisioned that the flavoring may be any flavoring known in the art suitable for use in strips, which are both edible and dissolvable. In one particular embodiment, the strips of the present invention includes flavoring having such flavors as cherry, citrus, cola, mango and pomegranate. It is further envisioned that the strips of the present invention may also include other additives including, for example, additives for the purposes of saliva stimulation, plasticizing, stabilizing, emulsifying, fillers, thickening, binding, coloring, sweetening, or acting as a surfactant.

Examples of essential vitamins and minerals that can be used in the dissolvable strip of the present invention as well as information on these compounds are provided herein as examples and the disclosure of these vitamins/minerals are not designed to be fully inclusive. Too little of just one vitamin may disturb the body's balance and cause health problems. But taking too many vitamins can also be dangerous. This is especially true of the fat-soluble vitamins A, D, E and K because it's harder for the body to get rid of any excess through urine—the most common way to eliminate waste products.

| Vitamins | | | | | |
| --- | --- | --- | --- | --- | --- |
| Good for | Signs of deficiency | RDA | Good sources | Poisoning | Destroyed by |
| Vitamin A (retinol) properties | | | | | |
| Eyesight, growth, appetite and taste. | Night-blindness. | 800 micrograms | Liver, fish-liver oil, carrots, green leafy vegetables, egg yolks, enriched margarine, milk products, yellow fruits. | This vitamin is fat-soluble and so is stored in the body for a long time, especially in pregnancy. An overdose may be dangerous. | Fatty acids. |
| Vitamin B1 (thiamine) properties | | | | | |
| Nervous system, digestion, muscles, heart, alcohol-damaged nerve tissues. | Tingling in fingers and toes, confusion, difficulties in maintaining balance, loss of appetite, exhaustion, weakened powers of concentration. | 1.4 mg | Liver, yeast, rice, wholemeal products, peanuts, pork, milk. | No danger. It dissolves in water, so any excess is passed in urine. | High temperatures, alcohol and coffee. |
| Vitamin B2 (riboflavin) properties | | | | | |
| Growth, skin, nails, hair, sensitive lips and tongue, eyesight, the breakdown of protein, fat and carbohydrate. | Itchy irritated eyes, itchy mucous membranes (nose/mouth/throat), itchy lips and skin. | 1.6 mg | Milk, liver, yeast, cheese, green leafy vegetables, fish. | No danger. It dissolves in water, so any excess is passed in urine. | Alcohol and light (this is why milk-cartons are better than bottles). |
| Vitamin B6 (pyridoxine) properties | | | | | |
| Preventing skin conditions, nerve problems, helps the body absorb protein and carbohydrate. | Skin inflammation. | 2 mg-women taking the contraceptive pill may need more. | Fish, bananas, chicken, pork, wholegrains, dried beans. | May cause nerve problems in large doses. Evidence is conflicting about the maximum safe dose, so get medical advice before exceeding the RDA. | The contraceptive pill, roasted or boiled food, alcohol and estrogen (the female hormone). |

-continued

Vitamins

| Good for | Signs of deficiency | RDA | Good sources | Poisoning | Destroyed by |
|---|---|---|---|---|---|
| Vitamin B12 (cobalamin) properties | | | | | |
| Making red blood and the formation of the nerves. | Tiredness, breathing difficulties, dizziness, abnormalities in nerve tissue function. | 1 microgram | Fish, liver, beef, pork, milk, cheese. | No danger. It dissolves in water, so any excess is passed in urine. | Water, sunlight, alcohol, estrogen and sleeping pills |
| Vitamin C (ascorbic acid) properties | | | | | |
| Immune defense system, protection from viruses and bacteria, healing wounds, reducing cholesterol, cell lifespan, preventing scurvy. It's also a natural laxative. | Tiredness, bleeding gums, slow-healing wounds. | 60 mg | Citrus fruits, kiwi fruit, berries, tomatoes, cauliflower, potatoes, green leafy vegetables, peppers. | Large doses can cause diarrhea and nausea. Some scientists have argued that 1000-5000 mg per day may damage your DNA. | Boiling food, light, smoking and heat. |
| Vitamin D properties | | | | | |
| Strong bones and teeth | Unhealthy teeth, osteomalacia (causes weakening of bones), rickets in children. | 5 micrograms | Sunlight (the action of sunlight on the skin allows our bodies to manufacture vitamin D), cod-liver oil, sardines, herring, salmon, tuna, milk and milk products. | This vitamin is fat-soluble so can accumulate in the body. Overdoses are dangerous. | Mineral oil. |
| Vitamin E (tocopherol) properties | | | | | |
| Fighting toxins-vitamin E is a powerful antioxidant. | Weak muscles and fertility problems. | 10 mg | Nuts, soya beans, vegetable oil, broccoli, sprouts, spinach, wholemeal products, eggs. | There is a slight risk of overdose, because vitamin E is fat soluble. | Heat, oxygen, frost, iron, chlorine and mineral oil. |
| Folic acid properties | | | | | |
| Production of red blood cells. It is essential in the first three months of pregnancy to prevent birth defects such as spina bifida, cleft palate or cleft lip. | Tiredness due to anaemia, red tongue. | 200 micrograms. Women planning to conceive should take a daily supplement of 400 mcg, continued for the first 12 weeks of pregnancy. | Carrots, yeast, liver, egg, yolks, melon, apricots, pumpkin, avocado, beans, rye and wholewheat, green leafy vegetables. | No danger. It dissolves in water, so any excess is passed in urine. | Water, sunlight, estrogen, heat. |

Minerals

| Good for | Signs of deficiency | RDA | Good sources | Poisoning |
|---|---|---|---|---|
| Calcium | | | | |
| Strong bones and teeth, nerve function, muscle contraction, blood clotting. | Poor teeth and brittle bones. | 800 mg | Milk, cheese, butter, yoghurt and green leafy vegetables. | High doses can lead to headaches, stomach pain, high blood pressure and diarrhea. Excess calcium can be deposited as kidney and gall bladder stones. |
| Iron | | | | |
| Red blood cells and muscle function, white blood cells and the immune system. | Tiredness, irritability, difficulties concentrating | 14 mg | Lean red meat, oily fish, egg yolks, green leafy vegetables, nuts, wholegrains and wholewheat. | Iron is stored in the body and high doses (over 17 mg) can lead to constipation, vomiting, nausea and diarrhea. Very high doses can be fatal. |
| Magnesium | | | | |
| Converting energy from food, cell repair, building strong bones, teeth and muscles, regulating body temperature. | Muscle spasms, and has been associated with heart disease, diabetes, high blood pressure and weak bones. | 300 mg | Green leafy vegetables, wholegrains and nuts. | High doses can cause diarrhea. |

-continued

Minerals

| Good for | Signs of deficiency | RDA | Good sources | Poisoning |
|---|---|---|---|---|
| | | Zinc | | |
| Immune system, the breakdown of protein, fat and carbohydrate. | Lesions on skin, eyes and in throat, loss of taste and smell, hair loss, diarrhea, slow healing of wounds, growth problems in children. | 15 mg | Meat, shellfish, milk brown rice and wholegrains. | High doses can lead to stomach cramps, nausea and vomiting |

The 10 most important minerals are calcium; iodine; iron; magnesium; phosphorus; copper; manganese; chromium; selenium; and zinc. These can be either part of the strip itself or coated as granular particles on the strip or powdered coated on the strip so as to provide the dosage needed for the individuals depending on the circumstances.

In one embodiment of the present invention the strips contain a composition that can be used to prevent and/or treat the systems of alcohol-induced hangovers. The composition contains at least one dietary supplements selected from the group consisting of: thiamine (mononitrate), riboflavin, niacin (amide), vitamin B6, pantothenate (d-cal pantothenate), vitamin C (as calcium ascorbate), vitamin B-12 (as cyanocobalamin) and biotin as part of or coated on at least one orally soluble strip. It is important that the strip be at least partially coated with powder/particulars to prevent said strip from adhering or sticking to other surfaces.

In a preferred embodiment of the present invention, the composition that can be used to prevent and/or treat the symptoms of alcohol induced hangovers comprises at least 1 active ingredient selected from the group consisting of about 200 mg to about 400 mg of Thiamine (mononitrate); about 5 mg to about 20 mg of Riboflavin; about 50 mg to about 100 mg of Niacin (amide); about 20 mg to about 40 mg of Vitamin $B_6$; about 15 mg to about 30 mg of Pantothenate (d-cal Panthothenate); about 100 mg to about 300 mg of Vitamin C; about 20 mg to about 40 mg of Vitamin B-12; and about 20 mg to about 70 mg of Biotin. In addition to the aforementioned composition, the strip may have pharmaceutically acceptable carriers and salts as part of or coated on the orally dissolvable strip or multiplicity of strips of the present invention.

An even more preferred orally dissolvable strip designed to prevent and/or treat the symptoms of alcohol induced hangovers comprises about 300 mg of Thiamine (mononitrate); about 15 mg of Riboflavin; about 75 mg of Niacin (amide); about 30 mg of Vitamin $B_6$; about 25 mg of Pantothenate (d-cal Panthothenate); about 200 mg of Vitamin C; about 30 mg of Vitamin B-12; and about 50 of Biotin. In addition to the aforementioned composition, the strip may have pharmaceutically acceptable carriers and salts as part of or coated on the orally dissolvable strip or multiplicity of strips of the present invention.

Also provided as part of the present invention is a method for preventing and/or treating hangover symptoms and/or supplementing the diet of a mammal comprising providing at least one orally-soluble strip described above and placing the orally dissolvable strip in the oral cavity of a mammal so that it can dissolve. Once the strip is placed in the oral cavity, a predetermined amount of time is allotted to allow for the entire strip to dissolve in the mouth of the mammal. These two steps can be repeated as necessary. The method used for preventing and/or treating symptoms of alcohol-induced hangovers the strips can be administered prior to consuming alcohol and/or after the alcohol is consumed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed:

1. A dietary supplement delivery system for a mammal comprising:
an orally soluble multi-stacked strip having at least one dietary supplement within the strip itself, said orally soluble multi-stacked strip being at least partially coated with a powder comprising particles, said powder being free of any dietary supplements and flavoring agents, said strip including an underside surface attached to a backing material, said underside surface comprising less powder than a top surface of said strip such that said underside surface is releasably mounted to said backing material in a package and said top surface is prevented from adhering or sticking to other surfaces.

2. The dietary supplement delivery system of claim 1 wherein said strip further comprises a starch, pectin and/or cellulose, wherein said strip dissolves when placed in an oral cavity of a mammal and bypasses first pass metabolism.

3. The dietary supplement delivery system of claim 1 wherein said at least one dietary supplement is selected from the group consisting of: thiamine, riboflavin, niacin, vitamin B6, pantothenate, vitamin C, vitamin B-12, biotin, vitamin D3, vitamin A, vitamin K, and combinations thereof.

4. The dietary supplement delivery system of claim 1 further comprising at least one additive selected from the group consisting of coloring agent, surfactant, pharmaceutically acceptable filler, and fragrance.

5. The dietary supplement delivery system of claim 2 wherein said dietary supplement is selected from the group consisting of thiamine, riboflavin, niacin, vitamin B6, pantothenate, vitamin C, vitamin B-12, biotin, vitamin D3, vitamin A, vitamin K, and combinations thereof.

6. The dietary supplement delivery system of claim 1, wherein said dietary supplement is selected from the group consisting of vitamin A, vitamin D3, vitamin C, vitamin B, vitamin E, vitamin K, and combinations thereof.

7. A dietary supplement delivery system for a mammal comprising:
a multi-stacked strip comprising at least one dietary supplement within the strip and a powder coating that is free of any dietary supplements and flavoring agents;
a backing material in a package configured to dispense single servings of said multi-stacked strip,
wherein said multi-stacked strip is releasably mounted to said backing material and said multi-stacked strip is dissolvable in an oral cavity of the mammal to release said dietary supplement, wherein an underside surface of said strip engages said backing material and comprises a first amount of said powder to prevent said strip from permanently adhering or sticking to said backing material, and wherein a top surface of said multi-stacked strip has a second amount of said powder that is greater than said first amount.

8. The dietary supplement delivery system of claim 7 wherein said multi-stacked strip further comprises starch, pectin and/or cellulose and said powder comprises an inactive ingredient selected from the group consisting of coloring agent, surfactant, pharmaceutically acceptable filler, fragrance, and a combination thereof.

9. The dietary supplement delivery system of claim 7 wherein said dietary supplement is selected from the group consisting of thiamine, riboflavin, niacin, vitamin B6, pantothenate, vitamin C, vitamin B-12, biotin, and combinations thereof.

10. A dietary supplement delivery system of claim 7 wherein said dietary supplement is selected from the group consisting of vitamin A, vitamin D3, vitamin C, vitamin B, vitamin E, vitamin K, and combinations thereof.

11. The dietary supplement delivery system of claim 1 wherein said strip comprises at least 2% of a reference daily intake (RDI) of the at least one dietary supplement.

12. The dietary supplement delivery system of claim 1 wherein said dietary supplement delivery system comprises a plurality of strips that are spaced apart from one another along said backing material.

13. The dietary supplement delivery system of claim 12 wherein said backing material is waxy.

14. The dietary supplement delivery system of claim 13, wherein said backing material is coiled within said package.

15. The dietary supplement delivery system of claim 14 wherein a first end of said strip extends through an opening in said package while said coiled backing material is rotatably disposed in said package.

16. A dietary supplement delivery system for a mammal comprising:
 a package; and
 a plurality of orally soluble multi-stacked strips each having at least one dietary supplement within the strip itself, said strips each comprising an underside surface and an opposite top surface that are each at least partially coated with a powder comprising at least one of dietary supplement, said powder being free of any flavoring agents, said underside surfaces each being attached to a waxy backing material such that said strips are spaced apart from one another along said backing material, said underside surfaces each comprising less of said powder than said top surfaces such that said underside surfaces are releasably mounted to said backing material in said package and said top surfaces are prevented from adhering or sticking to other surfaces.

17. The dietary supplement delivery system of claim 16 wherein:
 said backing material is coiled within said package; and
 a first end of said strip extends through an opening in said package while said coiled backing material is rotatably disposed in said package.

* * * * *